(12) United States Patent
Takagi et al.

(10) Patent No.: US 8,360,775 B2
(45) Date of Patent: Jan. 29, 2013

(54) WAX MODEL BASE FOR ABUTMENT OF DENTAL IMPLANT

(75) Inventors: Takamitsu Takagi, Itabashi-ku (JP); Yusuke Noguchi, Itabashi-ku (JP); Fumiya Sato, Itabashi-ku (JP); Tsuyoshi Noguchi, Itabashi-ku (JP); Ryosuke Ikeya, Itabashi-ku (JP); Yoshihiro Sakaguchi, Itabashi-ku (JP)

(73) Assignee: GC Corporation, Tokyo (JP)

( * ) Notice: Subject to any disclaimer, the term of this patent is extended or adjusted under 35 U.S.C. 154(b) by 373 days.

(21) Appl. No.: 12/716,596

(22) Filed: Mar. 3, 2010

(65) Prior Publication Data
US 2010/0227294 A1 Sep. 9, 2010

(30) Foreign Application Priority Data
Mar. 6, 2009 (JP) .................................. 2009-053847

(51) Int. Cl.
*A61C 11/00* (2006.01)
(52) U.S. Cl. .......................... 433/213; 433/34; 433/201.1
(58) Field of Classification Search .......... 433/171–176, 433/201.1, 213, 34; 249/54; 264/16–20; 425/2, 175
See application file for complete search history.

(56) References Cited

U.S. PATENT DOCUMENTS

| | | | | |
|---|---|---|---|---|
| 4,758,161 A | * | 7/1988 | Niznick | 433/173 |
| 5,281,140 A | * | 1/1994 | Niznick | 433/172 |
| 5,915,968 A | * | 6/1999 | Kirsch et al. | 433/173 |
| 6,168,436 B1 | * | 1/2001 | O'Brien | 433/173 |
| 6,280,195 B1 | * | 8/2001 | Broberg et al. | 433/201.1 |
| 6,283,752 B1 | * | 9/2001 | Kumar | 433/172 |

(Continued)

FOREIGN PATENT DOCUMENTS

| | | |
|---|---|---|
| EP | 1 920 729 A1 | 5/2008 |
| EP | 1 925 268 A1 | 5/2008 |
| JP | 2002-78719 A | 3/2002 |

(Continued)

OTHER PUBLICATIONS

Extended European Search Report issued Jul. 27, 2010, in Patent Application No. 10002085.8.

*Primary Examiner* — Cris L Rodriguez
*Assistant Examiner* — Hao D Mai
(74) *Attorney, Agent, or Firm* — Oblon, Spivak, McClelland, Maier & Neustadt, L.L.P.

(57) ABSTRACT

For proper fitness of a core portion of an abutment to a patient, a wax model base for an abutment of a dental implant includes an engagement portion 1 engaging with an implant fixture analog embedded in a gypsum model without rotation, a truncated conical portion 2, a building portion 4 provided directly on an inner peripheral edge of a ring-like first stepped portion 3, which is provided on an oral cavity inner side of the truncated conical portion 2, or through a cylindrical portion 4a having a low height to have a conical shape expanding toward the oral cavity inner side and have a cutoff portion 5 on an outer peripheral surface, a cylindrical portion 7 provided on an inner peripheral edge of a ring-like second stepped portion 6 provided on the building portion 4, and a screw hole 8 along a center axis of the base.

13 Claims, 2 Drawing Sheets

U.S. PATENT DOCUMENTS

| | | | |
|---|---|---|---|
| 7,249,949 B2* | 7/2007 | Carter | 433/173 |
| 7,341,454 B2* | 3/2008 | Balfour et al. | 433/173 |
| 7,632,095 B2* | 12/2009 | Ostman et al. | 433/172 |
| 2007/0037123 A1* | 2/2007 | Mansueto et al. | 433/173 |
| 2007/0190490 A1 | 8/2007 | Giorno | |
| 2008/0153066 A1 | 6/2008 | Schlussel et al. | |
| 2008/0261176 A1* | 10/2008 | Hurson | 433/174 |
| 2010/0196855 A1* | 8/2010 | Muller et al. | 433/193 |
| 2010/0311011 A1* | 12/2010 | Schwieder et al. | 433/172 |

FOREIGN PATENT DOCUMENTS

| | | |
|---|---|---|
| JP | 2002-95680 A | 4/2002 |
| JP | 2004-337190 A | 12/2004 |

* cited by examiner

2

WAX MODEL BASE FOR ABUTMENT OF DENTAL IMPLANT

BACKGROUND OF THE INVENTION

1. Field of the Invention

The present invention relates to a wax model base for an abutment of a dental implant. The wax model base is for producing a wax model used for producing an abutment in a dental implant treatment, where the abutment has a core portion and a portion coming into contact with a gingiva suitable for a patient.

2. Description of the Conventional Art

A treatment technique of a dental implant has been conventionally developed and used as a dental prosthesis method at a lost tooth position, in addition to a method using a bridge or a denture. In the treatment technique of a dental implant, an implant fixture to be a device for retaining and stabilizing a dental prosthesis is embedded in an embedding hole formed in a jawbone at the lost tooth position, and substitutes it for a function of a dental root in a natural tooth. A dental prosthesis fixing device is connected and fixed on the oral cavity inner side of the implant fixture to make it to be a dental prosthesis retaining device. Then, a dental prosthesis is fixed to the dental prosthesis retaining device.

The implant treatment technique generally uses an abutment for a dental implant (it will be hereinafter called just an abutment) as the dental prosthesis fixing device connected and fixed to the oral cavity inner side of the implant fixture, where the abutment has a portion coming into contact with a gingiva and a fixing device of a dental prosthesis. The conventional abutment has an engagement portion for engaging with the implant fixture embedded in a jawbone at a lost tooth position so as not to rotate and has a through hole and the like to be fixed with a screw. A dental prosthesis is fixed thereto with a screw or cement or the like. An external shape of a portion to be the dental prosthesis fixing device of the conventional abutment has an approximately cylindrical shape or a truncated conical shape. When an angle is different between the implant fixture and the dental prosthesis, there are many shapes of abutment such as an abutment having an angle, etc.

For example, Japanese Patent Application Laid-Open No. 2004-337190, Japanese Patent Application Laid-Open No. 2002-78719 and Japanese Patent Application Laid-Open No. 2002-95680 discuss the conventional abutments having predetermined sizes and shapes. In addition to these, there is a custom abutment having a shape in which a portion coming into contact with a gingiva is fit for a gingival shape of an individual patient. A general production method of the custom abutment includes steps of making a wax model of the custom abutment with a wax so as to make a portion in contact with a gingiva in a shape fit for a gingival shape of an individual patient on a gypsum model reproducing an inside of an oral cavity in which the implant fixture is embedded, and cutting a pure-titanium metal or a titanium alloy by a CAD/CAM system based on the wax model to produce the custom abutment made of a pure-titanium metal or a titanium alloy. At this time, an implant fixture analog produced to have the same shape as a shape at the oral cavity inner side of the implant fixture is embedded at a position corresponding to a position in the gypsum model at which the implant fixture is embedded. By using this gypsum model, wax is built on a metal base (it is called a waxing base) corresponding to an engagement portion of the implant fixture analog.

However, in the waxing base discussed in each of aforementioned Japanese Patent Application Laid-Open No. 2004-337190, Japanese Patent Application Laid-Open No. 2002-78719 and Japanese Patent Application Laid-Open No. 2002-95680, it is not considered that the portion coming into contact with a gingiva is to be formed so as to have a shape fit for a gingival shape of an individual patient. In addition, as for the waxing base, an external shape of the portion to be the dental prosthesis fixing device is an approximately cylindrical shape or a truncated conical shape. Thus, a model for a portion to be a dental prosthesis is produced separately using wax, and there is a defect that a time and a workload are thus necessary.

SUMMARY OF THE INVENTION

Problem to be Solved by the Invention

The present invention is directed to a wax model base for an abutment of a dental implant capable of forming a portion coming into contact with a gingiva to have a shape fit for a gingival shape of an individual patient, and capable of producing a wax model in which a portion to be a dental prosthesis fixing device is formed with wax at once inclusive of a core portion similar to a dental prosthesis.

Means for Solving the Problem

Present inventors carried out earnest works to solve the aforementioned problems, and as a result, they found out the followings to complete the present invention. A wax model base for an abutment of a dental implant includes an engagement portion, a truncated conical portion, a ring-like first stepped portion, a conical building portion, a cutoff portion, a ring-like second stepped portion, and a cylindrical portion. The engagement portion engages with a locking portion for an abutment so as not to rotate, where the locking portion for an abutment is provided at the oral cavity inner side of a female screw provided along a center axis of an implant fixture analog. The implant fixture analog is embedded in a gypsum model reproducing the inside of an oral cavity in which an implant fixture is embedded in a jawbone at a lost tooth position. The truncated conical portion is fitted into a conical portion which is provided on the oral cavity inner side of the locking portion for an abutment and expands toward an oral cavity inner side thereof. The ring-like first stepped portion is provided on the oral cavity inner side of the truncated conical portion. The conical building portion is provided at the oral cavity inner side from an inner peripheral edge of the first stepped portion directly or through a cylindrical portion having a low height, and expands toward an oral cavity inner side thereof. The cutoff portion is provided on the outer peripheral surface at the oral cavity inner side of the building portion. The ring-like second stepped portion is provided on the oral cavity inner side of the building portion. The cylindrical portion is provided toward the oral cavity inner side from an inner peripheral edge of the second stepped portion. The wax model base for an abutment of a dental implant further includes a screw hole provided penetrating the wax model base along a center axis of the wax model base. The screw hole has a stepped portion at a middle position between a hole at the oral cavity inner side and a hole at the side opposite to the oral cavity inner side, where the hole at the oral cavity inner side has a large diameter, and the hole at the side opposite to the oral cavity inner side has a small diameter.

The engagement portion engages with the locking portion for an abutment so as not to rotate, where the locking portion for an abutment is provided on the oral cavity inner side of an implant fixture. The truncated conical portion is fitted into a conical portion which is provided on the oral cavity inner side of the locking portion for an abutment and expands toward an oral cavity inner side. Thus, each of the engagement portion and the truncated conical portion has a predetermined shape. Therefore, when a block made of pure-titanium, titanium alloy, or ceramics is prepared to have the previously determined shapes of the engagement portion, the truncated conical portion, and the penetrating screw hole, the same shape can be constantly obtained for each of the engagement portion, the truncated conical portion, and the penetrating screw hole. Then, a wax model is produced by forming a portion coming into contact with a gingiva at the oral cavity inner side from the truncated conical portion, so as to have a shape fit for a gingival shape of an individual patient, and forming with wax a portion to come to be a dental prosthesis fixing device at once inclusive of a core portion similar to a dental prosthesis except for a coping portion. The formed wax model is set to a three-dimensional measuring apparatus so as to obtain three-dimensional data of an external shape of the portion in which the wax is built. Finally, the block is machined the shape of abutment with in the same shape of wax model by a CAM device. As a result, an abutment can be produced easily to have a portion coming into a contact with a gingiva in a shape fit for a gingival shape of an individual patient, and a core portion similar to a dental prosthesis.

According to an aspect of the present invention, the present invention is a wax model base for an abutment of a dental implant, which includes an engagement portion engaging with a locking portion for an abutment so as not to rotate, where the locking portion for an abutment is provided at the oral cavity inner side of a female screw provided along a center axis of an implant fixture analog embedded in a gypsum model reproducing the inside of an oral cavity in which an implant fixture is embedded in a jawbone at a lost tooth position, a truncated conical portion fitted into a conical portion which is provided on the oral cavity inner side of the locking portion for an abutment and expands toward an oral cavity inner side thereof, a ring-like first stepped portion provided on the oral cavity inner side of the truncated conical portion, a conical building portion provided at the oral cavity inner side from an inner peripheral edge of the first stepped portion directly or through a cylindrical portion having a low height so as to expand toward an oral cavity inner side thereof, a cutoff portion provided on the outer peripheral surface at the oral cavity inner side of the building portion, a ring-like second stepped portion provided on the oral cavity inner side of the building portion, and a cylindrical portion provided at the oral cavity inner side from an inner peripheral edge of the second stepped portion, wherein the wax model base for an abutment of a dental implant further includes a screw hole provided penetrating the wax model base along a center axis of the wax model base, and the screw hole has a stepped portion formed at a middle position between a hole having a large diameter at the oral cavity inner side and a hole having a small diameter at the side opposite to the oral cavity inner side.

In the wax model base for an abutment of a dental implant, the truncated conical portion is preferably mirror-finished so as to be strongly fitted into the conical portion of the implant fixture which expands toward oral cavity inner side thereof. The building portion is preferably subjected to a surface roughening treatment such as sandblasting or the like so as to accurately fix the wax. Further, the cylindrical portion preferably has a concave groove provided near a center part in a height direction so that the core portion built with the wax could be strongly attached to an outer periphery of the cylindrical portion.

Effect of the Invention

A wax model base for an abutment of a dental implant according to the present invention includes an engagement portion engaging with a locking portion for an abutment so as not to rotate, where the locking portion for an abutment is provided at the oral cavity inner side of a female screw provided along a center axis of an implant fixture analog, and the implant fixture analog is provided in the same shape as an oral cavity inner side shape of the an implant fixture and is embedded at a position corresponding to a position at which the implant fixture is embedded, in a gypsum model reproducing the inside of an oral cavity in which the implant fixture is embedded in a jawbone at a lost tooth position, a truncated conical portion fitted into a conical portion which is provided on the oral cavity inner side of the locking portion for an abutment and expands toward an oral cavity inner side thereof, a ring-like first stepped portion provided on the oral cavity inner side of the truncated conical portion, a conical building portion provided at the oral cavity inner side from an inner peripheral edge of the first stepped portion directly or through a cylindrical portion having a low height, so as to expand toward an oral cavity inner side thereof, a cutoff portion provided on the outer peripheral surface at the oral cavity inner side of the building portion, a ring-like second stepped portion provided on the oral cavity inner side of the building portion, and a cylindrical portion provided at the oral cavity inner side from an inner peripheral edge of the second stepped portion, wherein the wax model base for an abutment of a dental implant further includes a screw hole provided penetrating the wax model base along a center axis of the wax model base, and the screw hole has a stepped portion at a middle position between a hole having a large diameter at the oral cavity inner side and a hole having a small diameter at the side opposite to the oral cavity inner side.

In the wax model base for an abutment of a dental implant having the above-mentioned structure, since the conical portion expanding toward the oral cavity inner side is provided on the oral cavity inner side of the engagement portion which engages with the locking portion for an abutment so as not to rotate, where the locking portion for an abutment is provided at the oral cavity inner side of the female screw provided along the center axis of the implant fixture analog, thus, even when a wax model to be produced is an abutment in which a portion coming into contact with a gingiva largely tapers and expands toward the oral cavity inner side, like a case of a molar tooth, the wax model base for an abutment of a dental implant can be sufficiently applied to such the abutment. Since the ring-like first stepped portion is provided on the oral cavity inner side of the truncated conical portion, wax built mainly for a portion corresponding to a portion coming into contact with a gingiva can be sufficiently supported. Since the truncated conical building portion expanding toward the oral cavity inner side thereof is provided at the oral cavity inner side from an inner peripheral edge of the first stepped portion directly or through a cylindrical portion having a low height, the portion corresponding to the portion coming into contact with a gingiva can be built with a few amount of wax. Since the cutoff portion is provided on the outer peripheral surface at the oral cavity inner side of the building portion, the built wax does not rotate. Since the ring-like second stepped portion is provided on the oral cavity inner side of the building portion, the wax having the shape of a core portion which is built at the oral cavity inner side from the building portion can be accurately supported. Since the cylindrical portion is provided at the oral cavity inner side from the inner peripheral edge of the second stepped portion, wax can be easily built on the outer periphery of the cylindrical portion so as to have the shape of a core portion.

Further, since the screw hole penetrating the wax model base is provided along a center axis of the wax model base from the cylindrical portion to the engagement portion, and the screw hole has the stepped portion at a middle position between a hole having a large diameter at the oral cavity inner side and a hole having a small diameter at the side opposite to the oral cavity inner side, when a wax model of an abutment is produced by using the wax model base for an abutment of a dental implant according to the present invention, the wax model base for an abutment of a dental implant can be fixed with a screw to the implant fixture analog.

In the wax model base for an abutment of a dental implant, if the truncated conical portion is mirror-finished, the wax model base can be strongly fitted into the conical portion of the implant fixture which expands toward the oral cavity inner side. If the building portion is subjected to a surface roughening treatment such as sandblasting or the like, the wax built to form the particularly important portion coming into contact with a gingiva can be accurately fixed. If the cylindrical portion has the concave shaped groove provided near a center part in the height direction, the core portion built with the wax can be strongly attached to an outer periphery of the cylindrical portion.

DETAILED DESCRIPTION OF PREFERRED EMBODIMENT

Figure 1:
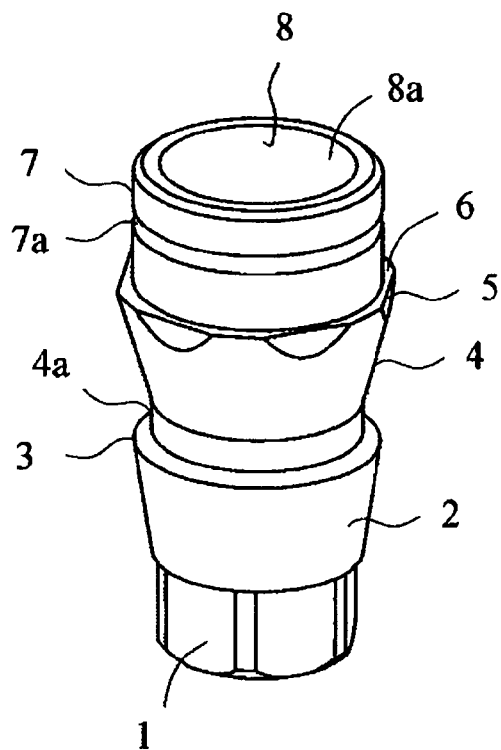
FIG. 1 is a perspective view of an exemplary embodiment of a wax model base for an abutment of a dental implant according to the present invention.
Figure 2:
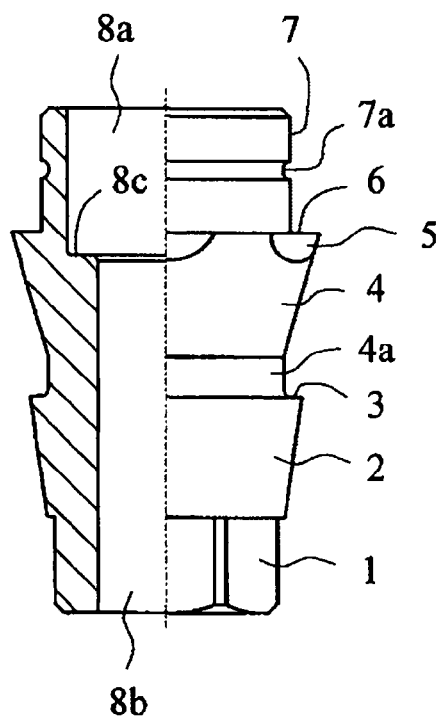
FIG. 2 is an explanatory view of the wax model base for an abutment of a dental implant according to the present invention in FIG. 1, illustrating the left half thereof by a sectional view and the right half by a side view.
Figure 3:
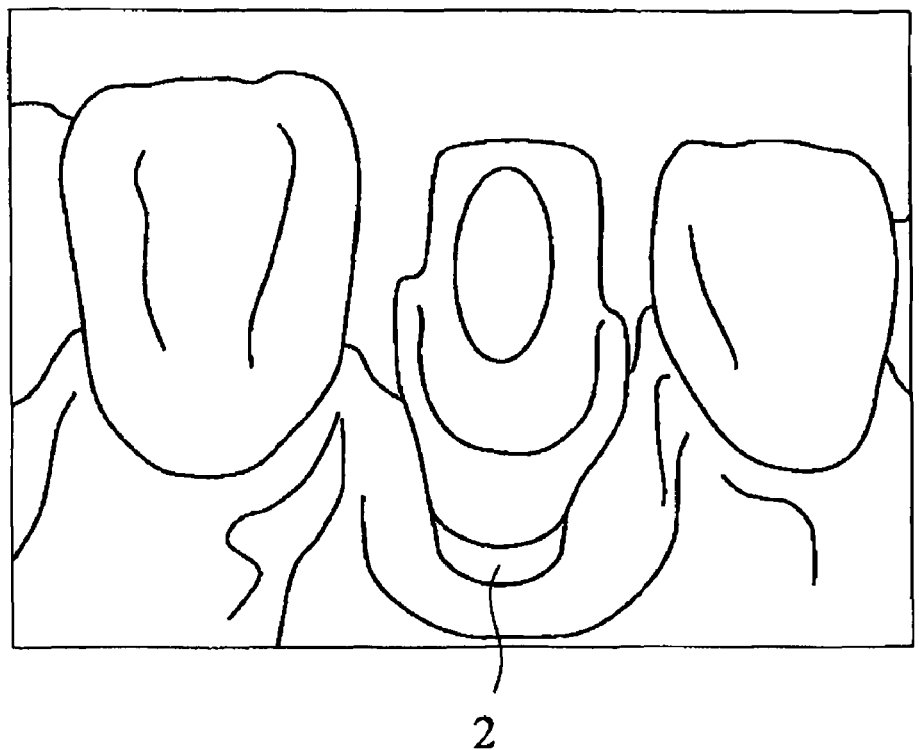
FIG. 3 is a perspective view of an exemplary embodiment of a wax model produced using a wax model base for an abutment of a dental implant according to the present invention, and mounted on a gypsum model in which an implant fixture analog is embedded.
Figure 4:
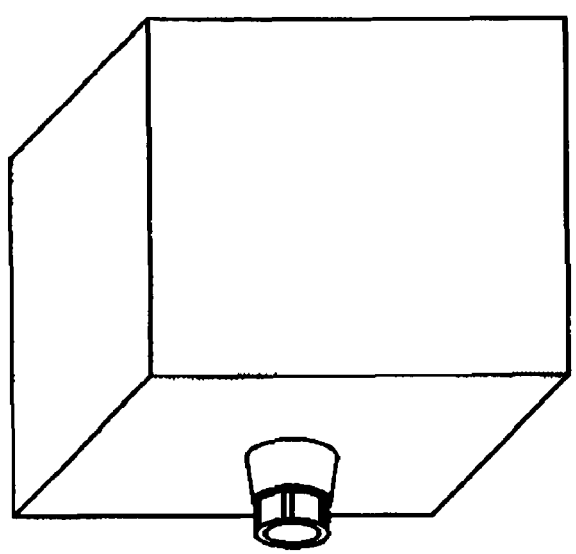
FIG. 4 is a perspective view of an exemplary embodiment of a block for cutting an abutment from the wax model produced using a wax model base for an abutment of a dental implant according to the present invention.

In the drawings, an engagement portion 1 engages with a locking portion for an abutment so as not to rotate. The locking portion for an abutment is provided at the oral cavity inner side of a female screw provided along a center axis of an implant fixture analog produced to have the same shape as a shape at the oral cavity inner side of an implant fixture embedded at a position corresponding to a position in gypsum model at which an implant fixture is embedded, where the gypsum model reproduces the inside of an oral cavity in which the implant fixture is embedded in a jawbone at a lost tooth position. The engagement portion 1 also engages with a locking portion for an abutment of the implant fixture so as not to rotate. The locking portion for an abutment of the implant fixture has the same shape as that of the locking portion for an abutment provided at the oral cavity inner side of the implant fixture analog. The engagement portion 1 is formed in a hexagonal shape having chamfered corner parts in the illustrated exemplary embodiment.

A truncated conical portion 2 is fitted into a conical portion which expands toward the oral cavity inner side, and is provided on the oral cavity inner side of the locking portion for an abutment of the implant fixture analog. The truncated conical portion 2 is also fitted into a conical portion of the implant fixture having the same shape as that of the conical portion provided at the oral cavity inner side of the implant fixture analog. Preferably, the truncated conical portion 2 is mirror-finished so as to be strongly fitted into the conical portion which is provided on the oral cavity inner side of the locking portion for an abutment of the implant fixture analog and expands toward the oral cavity inner side.

A ring-like first stepped portion 3 is provided on the oral cavity inner side of the truncated conical portion 2. The ring-like first stepped portion 3 is a portion to support wax to be built and to easily build the wax, even when the taper of the conical portion, which expands toward the oral cavity side, of a building portion 4 provided at the oral cavity inner side from an inner peripheral edge of the first stepped portion 3 as mentioned below, is large like a case of a molar tooth. Preferably, the ring-like first stepped portion 3 is formed to be a plane right-angled with respect to the center axis as illustrated in the figures.

The building portion 4 is provided from an inner peripheral edge of the first stepped portion 3 directly or through a cylindrical portion 4a having a low height at the oral cavity inner side. The building portion 4 has a truncated conical shape expanding toward oral cavity inner side. The building portion 4 is a portion to build wax mainly for a portion corresponding to a portion coming into contact with a gingiva, and comes to be a main portion (pillar) for supporting the wax built mainly for the portion corresponding to the portion coming into contact with a gingiva. The reason that the building portion 4 has the truncated conical shape is for reducing an amount of the wax to be built. The cylindrical portion 4a having a low height is provided preferably because the cylindrical portion 4a can securely fix the wax by interaction with the portion formed in the truncated conical shape, but the height of the cylindrical portion 4a is about 1 mm at the maximum. In addition, the building portion 4 is preferably subjected to a surface roughening treatment such as sandblasting or the like in order to securely fix the wax.

A cutoff portion 5 is provided on an outer peripheral surface at the oral cavity inner side of the building portion 4. The cutoff portion 5 prevents the built wax from rotating around the built portion 4. A shape of the cutoff portion 5 is not restricted to be a plane as illustrated in the figures, but can have a groove shape being parallel or inclining with respect to the center axis of the building portion 4.

A ring-like second stepped portion 6 is provided on the oral cavity inner side of the building portion 4. The ring-like second stepped portion 6 supports wax to be built in a shape of a core portion on an outer periphery of a cylindrical portion 7 mentioned below provided from an inner peripheral edge of the second stepped portion 6 toward the oral cavity inner side. Preferably, the ring-like second stepped portion 6 is formed to be a plane right-angled with respect to the center axis as illustrated in the figures.

The cylindrical portion 7 is provided from the inner peripheral edge of the second stepped portion toward the oral cavity inner side. On an outer periphery of the cylindrical portion 7, the wax is built to have the shape of the core portion. The core portion built with the wax on the outer periphery of the cylindrical portion 7 has a hole communicating with a hole 8a formed along the center axis of the cylindrical portion 7 to have a large diameter at the oral cavity inner side as mentioned below. In addition to this, when the cylindrical portion 7 has a concave groove 7a near a center part in a height direction of the outer periphery thereof, the core portion built with the wax can be surely mounted on the outer periphery of cylindrical portion 7, so it is preferable.

A screw hole 8 is formed penetrating along the center axis from the cylindrical portion 7 to the engagement portion 1, and has a stepped portion 8b at a middle position between the hole 8a having a large diameter at the oral cavity inner side and a hole 8b having a small diameter at the side opposite to the oral cavity inner side. A screw for fixing the wax model base for an abutment of a dental implant according to the present invention to the implant fixture analog is inserted and penetrated into the screw hole 8. In addition to this, the stepped portion 8c at the middle is a portion coming into contact with a head of the screw for fixing the wax model base for an abutment of a dental implant according to the present invention to the implant fixture analog.

A block 9 is made of pure-titanium, titanium alloy, or ceramic, and is for cutting an abutment from the wax model produced by using the wax model base for an abutment of a dental implant according to the present invention. The block 9 previously has a portion having the same shapes as the shapes of the engagement portion 1 and the truncated conical portion 2 of the wax model base for an abutment of a dental implant according to the present invention. In addition to this, the block 9 has a screw hole having the same shape as that of the screw hole 8 of the wax model base for an abutment of a dental implant according to the present invention. The screw hole of the block 9 is provided penetrating from the portion having the same shapes as those of the engagement portion 1 and the truncated conical portion 2 of the wax model base for an abutment of a dental implant according to the present invention toward a surface at the side opposite to these portions.

In order to produce the wax model of an abutment using the wax model base for an abutment of a dental implant according to the present invention, the engagement portion 1 of the wax model base for an abutment of a dental implant according to the present invention engages with the locking portion for an abutment provided at the oral cavity inner side of the female screw provided along the center axis of the implant fixture analog produced to have the same shape as the oral cavity inner side shape of the implant fixture embedded at the position corresponding to the position in the gypsum model at which the implant fixture is embedded, where the gypsum model reproduces the inside of an oral cavity in which the implant fixture is embedded in a jawbone at a lost tooth position. In addition to this, the truncated conical portion 2 is fitted into the conical portion expanding toward the oral cavity inner side and being provided on the oral cavity inner side of the locking portion for an abutment. A screw is inserted from the hole 8a side having a large diameter at the oral cavity inner side into the screw hole 8 formed penetrating along the center axis from the cylindrical portion 7 to the engagement portion 1. The screw is engaged with the female screw provided along the center axis of the implant fixture analog to fix the wax model base for an abutment of a dental implant according to the present invention to the implant fixture analog.

Then, wax is built on the ring-like first stepped portion 3 provided on the oral cavity inner side of the truncated conical portion 2 of the wax model base for an abutment of a dental implant according to the present invention, and is built on the outer periphery of the conical building portion 4 which expands toward the oral cavity inner side and is provided toward the oral cavity inner side from the inner peripheral edge of the first stepped portion 3 directly or through the cylindrical portion 4a having a low height. Particularly, the wax is built mainly for the portion corresponding to the portion coming into contact with a gingiva, while the rotation of the wax is prevented by the cutoff portion 5 provided on the outer peripheral surface at the oral cavity inner side of the building portion 4. In addition to this, wax is built on the ring-like second stepped portion 6 provided on the oral cavity inner side of the building portion 4, and on the outer surface of cylindrical portion 7 provided from the inner peripheral edge of the second stepped portion 6 toward the oral cavity inner side, and is built to have the shape of the core portion at the occlusal surface side.

Then, a driver is inserted into the screw hole 8 from the oral cavity inner side of the core portion, to remove the screw fixing the wax model to the implant fixture analog, where the wax model is produced by using the wax model base for an abutment of a dental implant according to the present invention. The wax model is removed from the implant fixture analog, and is set to a three-dimensional measuring apparatus to obtain three-dimensional data of an external shape of a portion built with wax. Then, the block 9 is machined the shape of abutment with in the same shape of wax model by a CAM device. Accordingly, an abutment can be produced easily to have a portion coming into contact with a gingiva in a shape fit for a gingival shape of an individual patient, and to have a core portion similar to a dental prosthesis.

When the abutment is thus produced, a coping is bonded to the core portion of the abutment and fixed to the implant fixture, which is embedded in a jawbone at a lost tooth position, with a screw. As a result, the implant treatment is completed.

What is claimed is:

1. A wax model base for an abutment of a dental implant comprising:
    an engagement portion engaging with a locking portion for an abutment so as not to rotate, wherein the locking portion for an abutment is provided at an oral cavity inner side of a female screw provided along a center axis of an implant fixture analog embedded in a gypsum model reproducing an oral cavity in which an implant fixture is embedded in a jawbone at a lost tooth position;
    a truncated conical portion fitted into a conical portion which is provided on the oral cavity inner side of the locking portion for an abutment and expands outwardly toward the oral cavity inner side;
    a ring-like first stepped portion provided on the oral cavity inner side of the truncated conical portion;
    a conical building portion provided at the oral cavity inner side from an inner peripheral edge of the first stepped portion directly or through a cylindrical portion having a low height, so as to expand toward the oral cavity inner side;
    a cutoff portion provided on the outer peripheral surface at the oral cavity inner side of the building portion;
    a ring-like second stepped portion provided on the oral cavity inner side of the building portion;
    a cylindrical portion provided at the oral cavity inner side from an inner peripheral edge of the second stepped portion; and
    a screw hole provided penetrating along a center axis of the wax model base, and having a stepped portion formed at a middle position between a hole having a large diameter at the oral cavity inner side and a hole having a small diameter at the side opposite to the oral cavity inner side.

2. The wax model base for an abutment of a dental implant as claimed in claim 1, wherein the truncated conical portion is mirror-finished.

3. The wax model base for an abutment of a dental implant as claimed in claim 1, wherein the building portion is subjected to a surface roughening treatment.

4. The wax model base for an abutment of a dental implant as claimed in claim 2, wherein the building portion is subjected to a surface roughening treatment.

5. The wax model base for an abutment of a dental implant as claimed in claim 1, wherein the wax model base further comprises a concave groove near a center part in a height direction of the cylindrical portion.

6. The wax model base for an abutment of a dental implant as claimed in claim 2, wherein the wax model base further comprises a concave groove near a center part in a height direction of the cylindrical portion.

7. The wax model base for an abutment of a dental implant as claimed in claim 3, wherein the wax model base further comprises a concave groove near a center part in a height direction of the cylindrical portion.

8. The wax model base for an abutment of a dental implant as claimed in claim 4, wherein the wax model base further comprises a concave groove near a center part in a height direction of the cylindrical portion.

9. The wax model base for an abutment of a dental implant as claimed in claim 1, wherein the engagement portion has a hexagonal shape.

10. The wax model base for an abutment of a dental implant as claimed in claim 9, wherein the hexagonal shape has chamfered corner parts.

11. The wax model base for an abutment of a dental implant as claimed in claim 1, wherein the ring-like first stepped portion forms a plane oriented at a right angle with respect to the center axis of the dental implant.

12. The wax model base for an abutment of a dental implant as claimed in claim 1, wherein the cutoff portion has a groove in a parallel or inclining orientation with respect to a center axis of the conical building portion.

13. The wax model base for an abutment of a dental implant as claimed in claim 1, wherein the ring-like second stepped portion is oriented at a right angle with respect to the center axis of the dental implant.

* * * * *